(12) United States Patent
Zhang et al.

(10) Patent No.: US 10,694,975 B2
(45) Date of Patent: Jun. 30, 2020

(54) METHOD AND APPARATUS FOR RADIO-FREQUENCY POWER CALCULATION FOR MAGNETIC RESONANCE IMAGING

(71) Applicant: Siemens Healthcare GmbH, Erlangen (DE)

(72) Inventors: Qiu Yi Zhang, Shenzhen (CN); Qi Xing Chen, Shenzhen (CN); Jian Zhang Jia, Shenzhen (CN); Li Bo Sun, Shenzhen (CN)

(73) Assignee: Siemens Healthcare GmbH, Erlangen (DE)

( * ) Notice: Subject to any disclaimer, the term of this patent is extended or adjusted under 35 U.S.C. 154(b) by 573 days.

(21) Appl. No.: 15/365,132

(22) Filed: Nov. 30, 2016

(65) Prior Publication Data

US 2017/0153309 A1 Jun. 1, 2017

(30) Foreign Application Priority Data

Nov. 30, 2015 (CN) .......................... 2015 1 0848382

(51) Int. Cl.
*A61B 5/055* (2006.01)
*G01R 33/54* (2006.01)
*G01R 33/28* (2006.01)
*G01R 33/36* (2006.01)
*A61B 5/00* (2006.01)

(52) U.S. Cl.
CPC ............ *A61B 5/055* (2013.01); *G01R 33/288* (2013.01); *G01R 33/36* (2013.01); *G01R 33/3621* (2013.01); *G01R 33/543* (2013.01); *A61B 5/746* (2013.01); *A61B 2560/0276* (2013.01)

(58) Field of Classification Search
USPC .......................... 324/300–322; 600/407–435; 382/128–131
See application file for complete search history.

(56) References Cited

U.S. PATENT DOCUMENTS

| 798,612 | A | | 9/1905 | Mariani | |
|---|---|---|---|---|---|
| 3,287,629 | A | * | 11/1966 | Varian | G01R 33/46 324/310 |
| 5,663,638 | A | | 9/1997 | Humpherys | |
| 7,292,830 | B1 | | 11/2007 | Cheung et al. | |
| 8,930,151 | B2 | * | 1/2015 | Nistler | G01R 33/36 702/60 |

(Continued)

FOREIGN PATENT DOCUMENTS

| CN | 101051851 A | 10/2007 |
|---|---|---|
| CN | 102142907 A | 8/2011 |

(Continued)

*Primary Examiner* — Dixomara Vargas
(74) *Attorney, Agent, or Firm* — Schiff Hardin LLP

(57) ABSTRACT

In an RF power calculation apparatus and method for an MRI system, a first power calculation processor calculates a first power of an RF signal received by a first receiving method, a second power calculation processor calculates a second power of the RF signal received by a second receiving method, a difference calculation processor calculates the difference between the first power and second power, an RF power calculation processor calculates an RF power of the RF signal on the basis of the first power and second power when the difference is smaller than a first threshold.

7 Claims, 9 Drawing Sheets

(56) References Cited

U.S. PATENT DOCUMENTS

| | | | | |
|---|---|---|---|---|
| 2011/0254545 A1* | 10/2011 | Gebhardt | ............ | G01R 33/288 |
| | | | | 324/307 |
| 2011/0295531 A1* | 12/2011 | Nistler | ................ | G01R 33/288 |
| | | | | 702/60 |
| 2015/0282095 A1 | 10/2015 | Wang et al. | | |
| 2017/0033893 A1* | 2/2017 | Kang | .................. | H04B 17/318 |
| 2017/0153309 A1* | 6/2017 | Zhang | .................... | G01R 33/54 |

FOREIGN PATENT DOCUMENTS

| CN | 102404831 A | 4/2012 |
|---|---|---|
| CN | 104753544 A | 7/2015 |
| CN | 104950272 A | 9/2015 |

\* cited by examiner

METHOD AND APPARATUS FOR RADIO-FREQUENCY POWER CALCULATION FOR MAGNETIC RESONANCE IMAGING

BACKGROUND OF THE INVENTION

Field of the Invention

The present invention concerns the technical field of medical equipment, in particular to a radio frequency power calculation apparatus and method for a magnetic resonance imaging system.

Description of the Prior Art

Magnetic resonance imaging (MRI) is an imaging technology involving biomagnetics and nuclear spin that has advanced rapidly with the development of computer technology, electronic circuit technology and superconductor technology. MRI uses a magnetic field and radio frequency (RF) pulses to induce oscillation of precessing hydrogen nuclei (i.e. H+) in human tissue, to generate RF signals which are processed by a computer to form an image. If an object is placed in a magnetic field and irradiated by suitable electromagnetic waves to produce resonance therein, and electromagnetic waves emitted thereby are then analysed, it is possible to learn the positions and types of the atomic nuclei of which the object is composed. On this basis, a precise three-dimensional image of the interior of the object can be generated. For instance, a moving picture of contiguous slices can be obtained by performing an MRI scan of the human brain.

Based on considerations of patient safety, during an MRI scan it is necessary to measure the power of RF signals in real time, to ensure that the RF signal power satisfies the corresponding safety specification. Once RF signals have been amplified, most of the RF signals are sent to a transmission coil via a directional coupler, with the remaining small number of RF signals being used for power measurement.

In the prior art, an RF signal used for power measurement is received by an RF signal receiving method, and the power value of the RF signal is calculated. However, the RF signal receiving method in the prior art is unitary, and cannot ensure patient safety, and the calculation results are inaccurate.

SUMMARY OF THE INVENTION

An object of the present invention is to provide an RF power calculation apparatus and method for an MRI system, so as to improve the accuracy of RF power calculation.

According to one aspect of the present invention, an RF power calculation apparatus for an MRI system has an input interface that receives an RF signal by a first receiving method (mode) and that receives the RF signal also by a second receiving method (mode), a first power calculation processor configured to calculate a first power of an RF signal received by the first receiving method, a second power calculation processor configured to calculate a second power of the RF signal received by the second receiving method, a difference calculation processor configured to calculate a difference between the first power and second power, and an RF power calculation processor configured to calculate an RF power of the RF signal on the basis of the first power and second power when the difference is smaller than a first threshold, and to emit an electronic signal representing the calculated RF power.

Preferably, the RF power calculation processor is configured to calculate an average value of the first power and second power to serve as the RF power, when the difference is smaller than the first threshold.

In an embodiment, the RF power calculation apparatus has an alarm module that issues a first alarm instruction when the difference is greater than or equal to the first threshold, or issues a second alarm instruction when the RF power is greater than a second threshold.

Preferably, the first receiving method is a narrow-band receiving method and the second receiving method is a wide-band receiving method, or the first receiving method is a narrow-band receiving method and the second receiving method is another narrow-band receiving method, or the first receiving method is a wide-band receiving method, and the second receiving method is another wide-band receiving method.

Preferably, the first receiving method is a narrow-band receiving method, and the second receiving method is a wide-band receiving method. In that case, the first power calculation processor has a center frequency identification processor configured to identify a center frequency of the RF signal, a frequency compensation processor configured to perform a frequency compensation on the RF signal whose center frequency has been identified, a down conversion processor configured to perform a down conversion on the RF signal that has undergone frequency compensation, and a power measurement value calculation processor configured to calculate a power of the RF signal that has undergone down conversion.

Preferably, the power measurement value calculation processor has an amplitude extraction element, a sliding average processing element, a non-linear correction element, and an RF power integral operation element, and the second power calculation module has a sliding average processing element, a non-linear correction element, and an RF power integral operation element.

According to another aspect of the present invention, an RF power calculation apparatus for an MRI system has an input interface that receives an RF signal by a first receiving method (mode) and that also receives the Rf signal by a second receiving method (mode) and that also receives the RF signal by a third receiving method (mode), a first power calculation processor configured to calculate a first power of an RF signal received by the first receiving method, a second power calculation processor configured to calculate a second power of the RF signal received by the second receiving method, a third power calculation processor configured to calculate a third power of the RF signal received by the third receiving method, a difference calculation processor configured to calculate a first difference between the first power and second power, a second difference between the first power and third power, and a third difference between the second power and third power, and an RF power calculation processor configured to calculate an RF power of the RF signal on the basis of the first power, second power and third power, when the first difference, second difference and third difference are all smaller than a first threshold.

Another aspect of the present invention is an RF power calculation method for an MRI system, having the steps of via an input interface to a computer, receiving an RF signal by a first receiving method (mode) and also receiving the RF signal by a second receiving method (mode) and, in said computer, calculating a first power of an RF signal received by the first receiving method, calculating a second power of the RF signal received by the second receiving method, calculating a difference between the first power and second power, calculating an RF power of the RF signal on the basis of the first power and second power when the difference is smaller than a first threshold, and making the calculated RF power available from the processor as an electrical signal.

Preferably, the first receiving method is a narrow-band receiving method and the second receiving method is a wide-band receiving method, or the first receiving method is a narrow-band receiving method and the second receiving method is another narrow-band receiving method, or the first receiving method is a wide-band receiving method and the second receiving method is another wide-band receiving method.

According to another aspect of the present invention, an RF power calculation method for an MRI system has the steps of, via an input interface to a computer, receiving an RF signal by a first receiving method (mode) and also receiving the RF signal by a second receiving method (mode) and also receiving the RF signal by a third receiving method (mode) and, in said computer, calculating a first power of an RF signal received by the first receiving method, calculating a second power of the RF signal received by the second receiving method, calculating a third power of the RF signal received by the third receiving method, calculating a first difference between the first power and second power, a second difference between the first power and third power, and a third difference between the second power and third power, and calculating an RF power of the RF signal on the basis of the first power, second power and third power, when the first difference, second difference and third difference are all smaller than a first threshold, and making the calculated RF power available from the processor as an electrical signal.

It can be seen from the technical solution described above that, in an embodiment of the present invention, a first power calculation processor configured to calculate a first power of an RF signal received by the first receiving method, a second power calculation processor configured to calculate a second power of the RF signal received by the second receiving method, a difference calculation processor configured to calculate the difference between the first power and second power, an RF power calculation processor configured to calculate an RF power of the RF signal on the basis of the first power and second power, when the difference is smaller than a first threshold. The present invention compares the difference between the first power and second power, and when the difference is smaller than a first threshold, calculates a power of the RF signal on the basis of the first power and second power, and so can improve the accuracy of calculation.

Moreover, when the receiver is not operating normally and the power measurement value is not normal, an alert can be issued to the user promptly, thereby improving safety. Furthermore, the present invention employs multiple digital processing methods in the course of RF signal reception and processing, therefore the performance requirements for the analog front end are significantly reduced, and costs can thereby be saved.

DESCRIPTION OF THE PREFERRED EMBODIMENTS

The present invention is described in detail below in conjunction with the accompanying drawings and embodiments, to explain the technical solution and advantages thereof. It should be understood that the particular embodiments described herein are merely intended to explain the present invention elaboratively, not to define the scope of protection thereof.

The solution of the present invention is expounded below by describing a number of representative embodiments, in order to make the description concise and intuitive. The large number of details in the embodiments are merely intended to assist with understanding of the solution of the present invention. However, obviously, the technical solution of the present invention need not be limited to these details when implemented. To avoid making the solution of the present invention confused unnecessarily, some embodiments are not described meticulously, but merely outlined. Hereinbelow, "comprises" means "including but not limited to", while "according to . . . " means "at least according to . . . , but not limited to only according to . . . ". In cases where the quantity of a component is not specified hereinbelow, this means that there may be one or more of the component; this may also be interpreted as meaning at least one.

Figure 1:
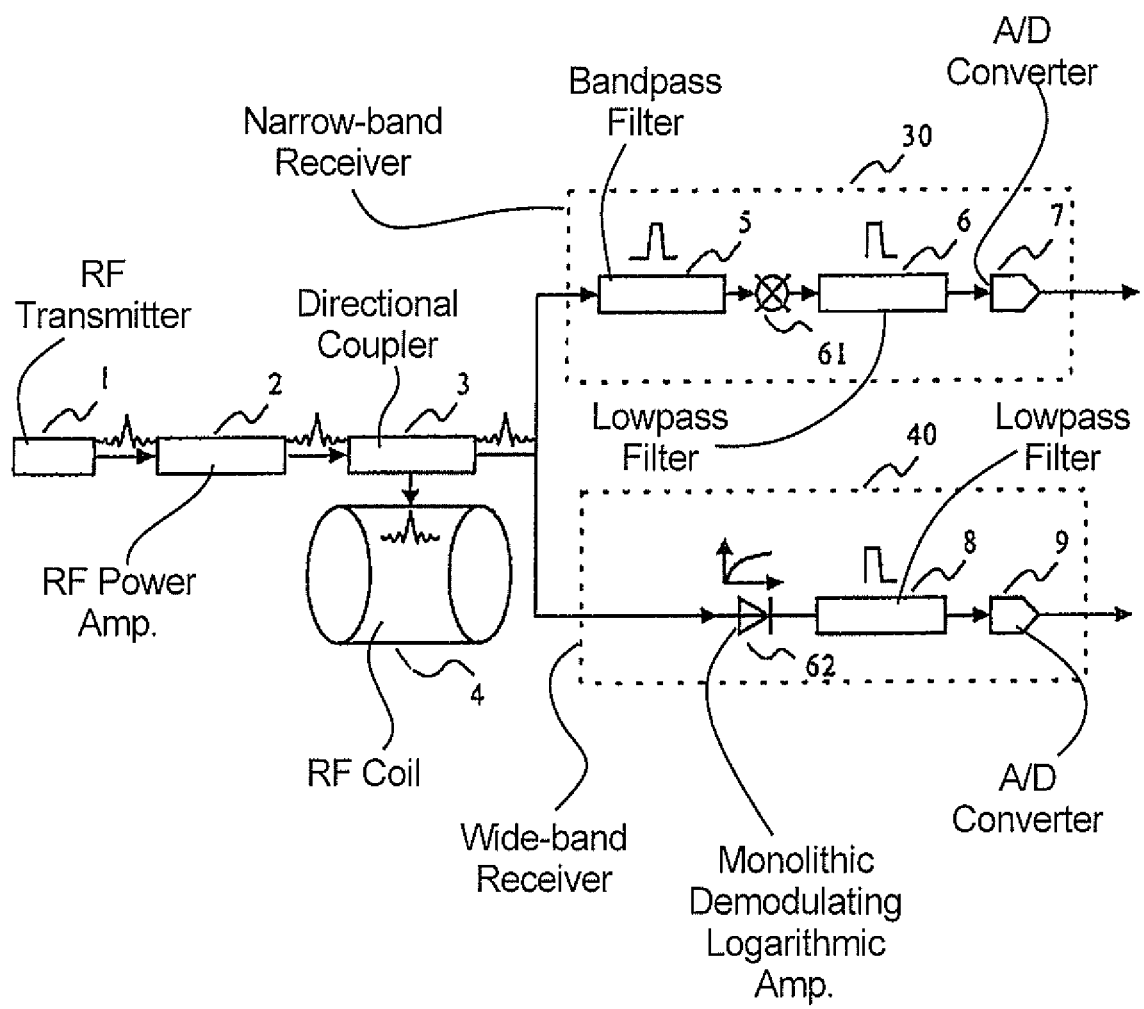
FIG. 1 is an analog front-end demonstrative processing schematic diagram of a power measurement process of an MRI system according to an embodiment of the present invention.

FIG. 1 is an analog front-end demonstrative processing schematic diagram of a power measurement process of an MRI system according to an embodiment of the present invention.

As FIG. 1 shows, the analog front end has an RF transmitter 1, an RF power amplifier 2, a directional coupler 3, a narrow-band receiver 30 and a wide-band receiver 40.

The RF transmitter 1 transmits RF signals in an analog signal format; the RF power amplifier 2 amplifies the RF signals in the analog signal format, and sends the amplified RF signals to the directional coupler 3; the directional coupler 3 sends most of the RF signals to an RF coil 4, so that the RF coil 4 transmits the RF signals. The directional coupler 3 also sends a small portion of RF signals to the narrow-band receiver 30 and the wide-band receiver 40, to be used for subsequent power measurement.

The narrow-band receiver 30 uses a narrow-band receiving method (mode) for receiving and converts the RF signals to a digital signal format. The narrow-band receiver 30 comprises a band-pass filter 5, a mixer 61, a low-pass filter 6 and an analog/digital converter 7.

The wide-band receiver 40 uses a wide-band receiving method (mode) for receiving and converts the RF signals to a digital signal format. The wide-band receiver 40 comprises a monolithic demodulating logarithmic amplifier 62, a low-pass filter 8 and an analog/digital converter 9.

RF signals received by the narrow-band receiver 30 by the narrow-band receiving method and RF signals received by the wide-band receiver 40 by the wide-band receiving method can serve as input signals for RF power measurement in the present invention.

Figure 2:
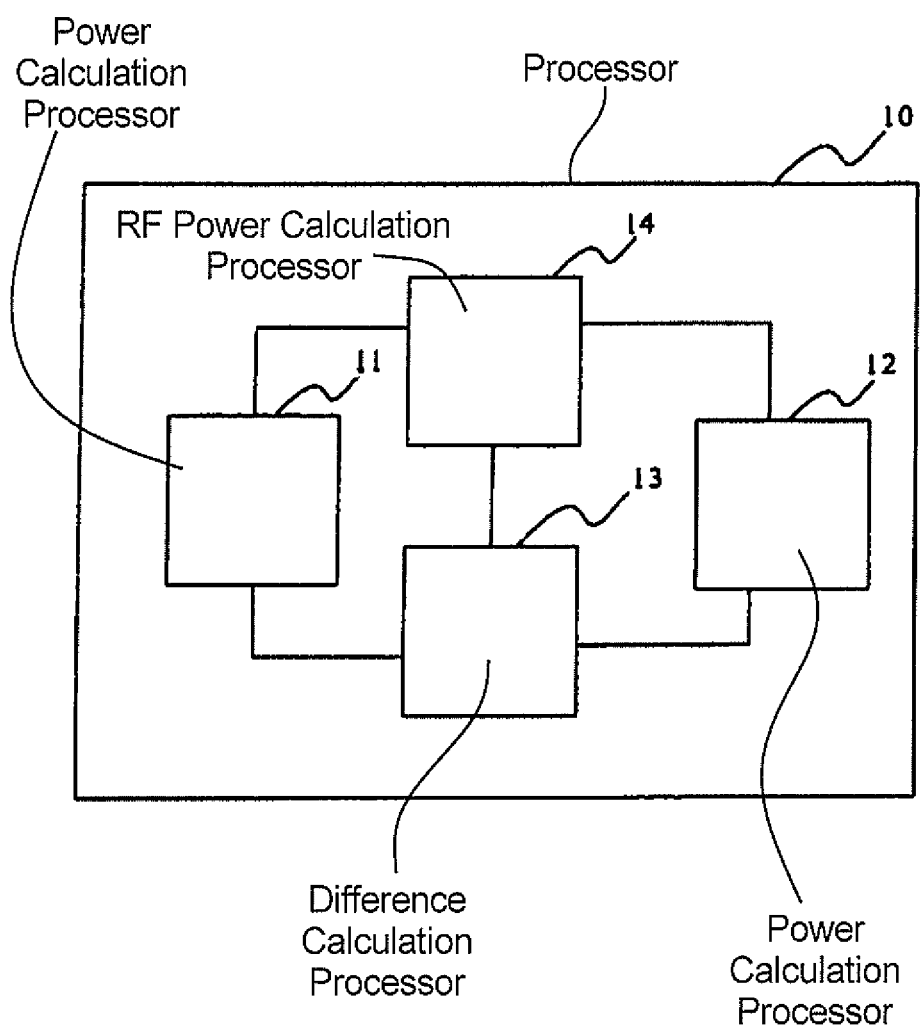
FIG. 2 is a block diagram of an RF power calculation apparatus for an MRI system according to an embodiment of the present invention.

FIG. 2 is a block diagram of an RF power calculation apparatus for an MRI system according to an embodiment of the present invention.

As FIG. 2 shows, the processor 10 has:

a first power calculation processor 11 that calculates a first power of an RF signal received by the first receiving method;

a second power calculation processor 12 that calculates a second power of the RF signal received by the second receiving method;

a difference calculation processor 13 that calculates the difference between the first power and second power;

an RF power calculation processor 14 that calculates an RF power of the RF signal on the basis of the first power and second power when the difference is smaller than a first threshold.

In one embodiment, the RF power calculation processor 14 calculates the average value of the first power and second power to serve as an RF power, when the difference is smaller than a first threshold. In another embodiment, the RF power calculation processor 14 calculates, on the basis of a weighting algorithm and according to a pre-set weighting of the first power and a pre-set weighting of the second power respectively, a weighted value of the first power and second power to serve as an RF power, when the difference is smaller than a first threshold. In another embodiment, the RF power calculation processor 14 calculates the square root of the sum of the squares of the first power and second power to serve as an RF power, when the difference is smaller than a first threshold.

The examples above describe typical practical examples of calculating an RF power of the RF signal according to the first power and second power, but those skilled in the art will realize that such description is demonstrative, and not intended to define the scope of protection of the present invention.

Specifically, an input end of the first power calculation processor 11 may be connected to a first receiver which receives an RF signal for power measurement from a directional coupler by a first receiving method. The first receiver performs analog/digital conversion, to convert the RF signal to a digital signal format. The first receiver then sends the RF signal in the digital signal format to the first power calculation processor 11, so that the first power calculation processor 11 calculates a first power of the RF signal in the digital signal format.

An input end of the second power calculation processor 12 may be connected to a second receiver which receives an RF signal for power measurement from a directional coupler by a second receiving method. The second receiver performs analog/digital conversion, to convert the RF signal to a digital signal format. In addition, the second receiver sends the RF signal in the digital signal format to the second power calculation processor 12, so that the second power calculation processor 12 calculates a second power of the RF signal in the digital signal format.

The RF signal received by the first receiver and the RF signal received by the second receiver originate from the same RF signal. In theory, the first power and second power are equal. However, due to the fact that the first receiver and second receiver are different, the first power and second power may in fact be different.

The difference calculation processor 13 calculates the difference between the first power and second power. When the difference between the first power and second power is smaller than a pre-set first threshold, it can be determined that the first receiver and second receiver are both operating normally; when the difference between the first power and second power is greater than or equal to the pre-set first threshold, it can be determined that at least one of the first receiver and second receiver is not operating normally.

For example, when the difference between the first power and second power is smaller than the pre-set first threshold, i.e. the first receiver and second receiver are both operating normally, the RF power calculation processor 14 calculates the average value of the first power and second power, and uses the average value as a power measurement value of the RF signal. Moreover, when the average value is no greater than a second threshold defined by a safety specification, it is determined that the RF signal power is normal; when the average value is greater than the second threshold defined by the safety specification, it is determined that the RF signal power is abnormal.

In one embodiment, the apparatus also has:

an alarm module that issues a first alarm instruction when the difference between the first power and second power is greater than or equal to the first threshold, or issues a second alarm instruction when the average value of the first power and second power is greater than the pre-set second threshold.

The first alarm instruction is for indicating to a user that at least one of the first receiver and second receiver is not operating normally. The second alarm instruction is for indicating to a user that the RF signal power does not conform to the safety specification.

In an embodiment, the first receiving method is a narrow-band receiving method, while the second receiving method is a wide-band receiving method. In the narrow-band receiving method, the narrow-band receiver may comprise: a band-pass filter; a mixer; a low-pass filter and an analog/digital converter. In the wide-band receiving method, the wide-band receiver may comprise: a monolithic demodulating logarithmic amplifier; a low-pass filter and an analog/digital converter.

In an embodiment, when the first receiving method is a narrow-band receiving method, and the first power calculation processor has a center frequency identification unit that identifies a center frequency of an RF signal, a frequency compensation unit that performs frequency compensation on the RF signal whose center frequency has been identified, a down conversion unit that performs down conversion on the RF signal that has undergone frequency compensation, and a power measurement value calculation unit that calculates a power of the RF signal that has undergone down conversion. Specifically, the power measurement value calculation unit has an amplitude extraction element, a sliding average processing element, a non-linear correction element, and an RF power integral operation element.

In an embodiment, when the second receiving method is a wide-band receiving method, the second power calculation processor has a sliding average processing element, a non-linear correction element, and an RF power integral operation element.

Preferably, parameters in the process of receiving and processing RF signals in the present invention are adjustable, so can be applied to more than one specific application environment. For instance, it is possible, according to the actual application, to periodically adjust a correction parameter of the non-linear correction element, a center frequency of the center frequency identification unit and a frequency compensation factor of the frequency compensation unit, therefore the present invention can achieve high-precision calibration, so as to better meet user demands.

The present invention may employ a wide-band receiving method and a narrow-band receiving method to receive an RF signal from an analog front end, or employ two narrow-band receiving methods or two wide-band receiving methods to receive an RF signal from an analog front end. For example: in one embodiment, the first receiving method is a narrow-band receiving method, while the second receiving method is another narrow-band receiving method. Alternatively, the first receiving method is a wide-band receiving method, while the second receiving method is another wide-band receiving method.

The present invention is explained below in greater detail by way of examples.

Figure 3:
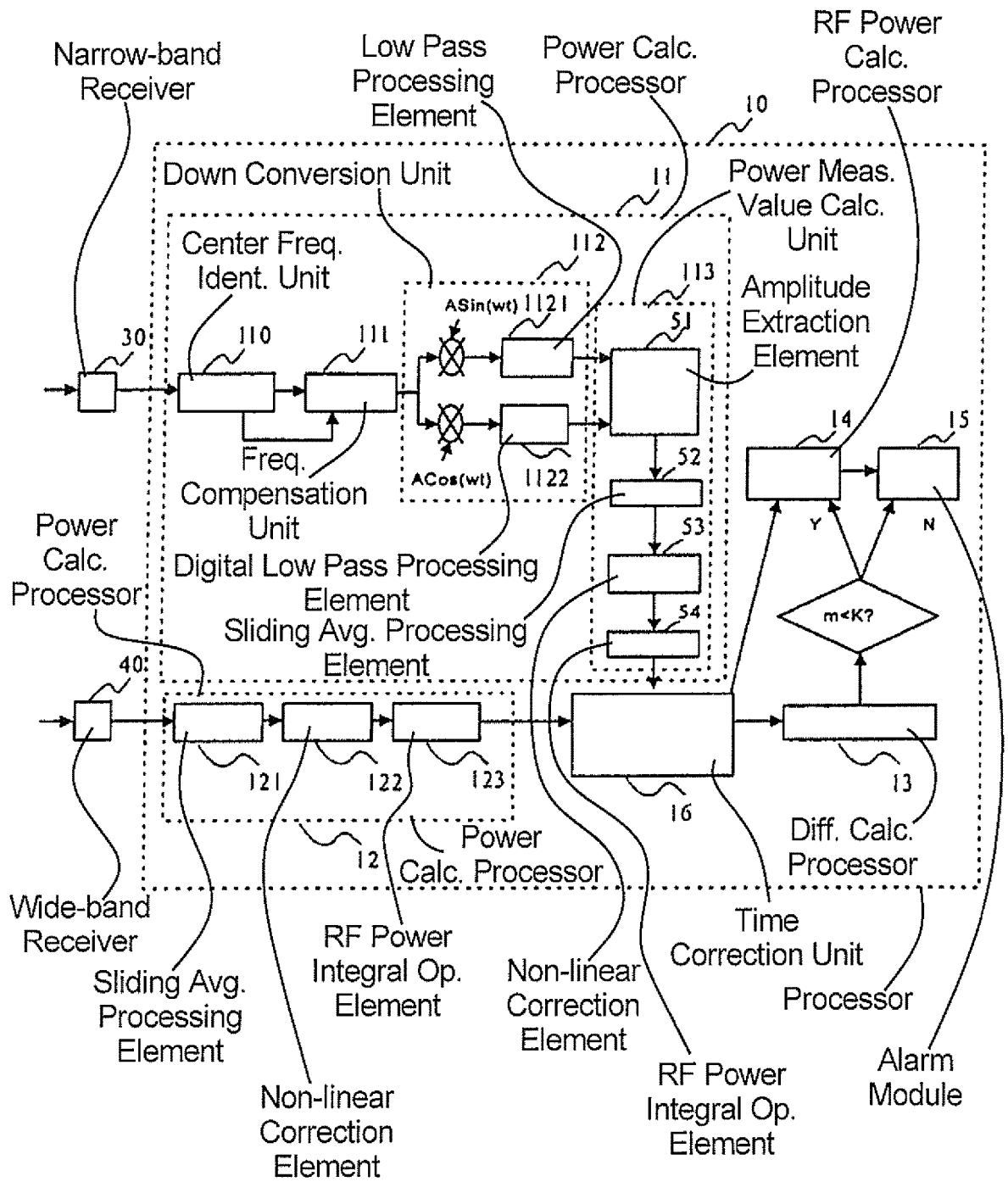
FIG. 3 is a block diagram of a first demonstrative application of the RF power calculation apparatus for an MRI system according to an embodiment of the present invention.

FIG. 3 is a block diagram of a first demonstrative application of an RF power calculation apparatus for an MRI system according to an embodiment of the present invention.

As FIG. 3 shows, the RF power calculation processor 10 has two input signals; one input signal is an RF signal received from the analog front end by means of a narrow-band receiver 30, the other input signal is an identical RF signal received from the analog front end by means of a wide-band receiver 40.

The RF signal received by the narrow-band receiver 30 is inputted to a first power calculation processor 11. The first power calculation processor 11 has a center frequency identification unit 110, a frequency compensation unit 111, a down conversion unit 112 and a power measurement value calculation unit 113. The center frequency identification unit 110 identifies a center frequency of an RF signal received by the narrow-band receiver 30; the frequency compensation unit 111 performs frequency compensation on the RF signal whose center frequency has been identified; the down conversion unit 112 performs down conversion on the RF signal that has undergone frequency compensation; and the power measurement value calculation unit 113 calculates a power of the RF signal that has undergone down conversion.

Specifically, the down conversion unit 112 has a multiplier A sin(wt), a multiplier A cos(wt), a digital low-pass processing element 1121 connected to the multiplier A sin(wt), and a digital low-pass processing element 1122 connected to the multipler A cos(wt). The power measurement value calculation unit 113 has an amplitude extraction element 51, a sliding average processing element 52, a non-linear correction element 53, and an RF power integral operation element 54. The amplitude extraction element 51 extracts an amplitude from the RF signal; the sliding average processing element 52 performs sliding average processing; the non-linear correction element 53 performs non-linear correction; the RF power integral operation element 54 calculates a power, i.e. a first power, of the RF signal received by the narrow-band receiving method by the narrow-band receiver 30.

The RF signal received by the wide-band receiver 40 is provided as an input to a second power calculation processor 12. The second power calculation processor 12 comprises: a sliding average processing element 121, a non-linear correction element 122 and an RF power integral operation element 123. The sliding average processing element 121 performs sliding average processing; the non-linear correction element 122 performs non-linear correction; the RF power integral operation element 123 calculates a power, i.e. a second power, of the RF signal received by the wide-band receiving method by the wide-band receiver 40.

A time correction unit 16 performs time correction on the first power and second power. A difference calculation processor 13 calculates the difference m between the first power and second power which have undergone time correction. When the difference m is smaller than a pre-set first threshold K, an RF power calculation processor 14 calculates the average value of the first power and second power, the average value being a measurement value of the RF signal. When the average value of the first power and second power is greater than a pre-set second threshold G, the RF power calculation processor 14 sends a trigger signal to an alarm module 15. When the difference m is not smaller than the pre-set first threshold K, the difference calculation processor 13 sends a trigger signal to the alarm module 15.

Upon receiving the trigger signal sent by the RF power calculation processor 14, the alarm module 15 issues to the user an alarm instruction indicating that the RF signal power does not conform to the safety specification. Moreover, when the alarm module 15 receives the trigger signal sent by the difference calculation processor 13, the alarm module 15 issues to the user an alarm instruction indicating that RF signal reception is abnormal.

In the embodiment shown in FIG. 3, identical RF signals are received by a narrow-band receiving method and a wide-band receiving method respectively, to serve as two input signals of the RF power calculation apparatus. In fact, it is also possible for identical RF signals to be received by a narrow-band receiving method and another narrow-band receiving method, to serve as two input signals of the RF power calculation apparatus, or for identical RF signals to be received by a wide-band receiving method and another wide-band receiving method, to serve as two input signals of the RF power calculation apparatus.

Figure 4:
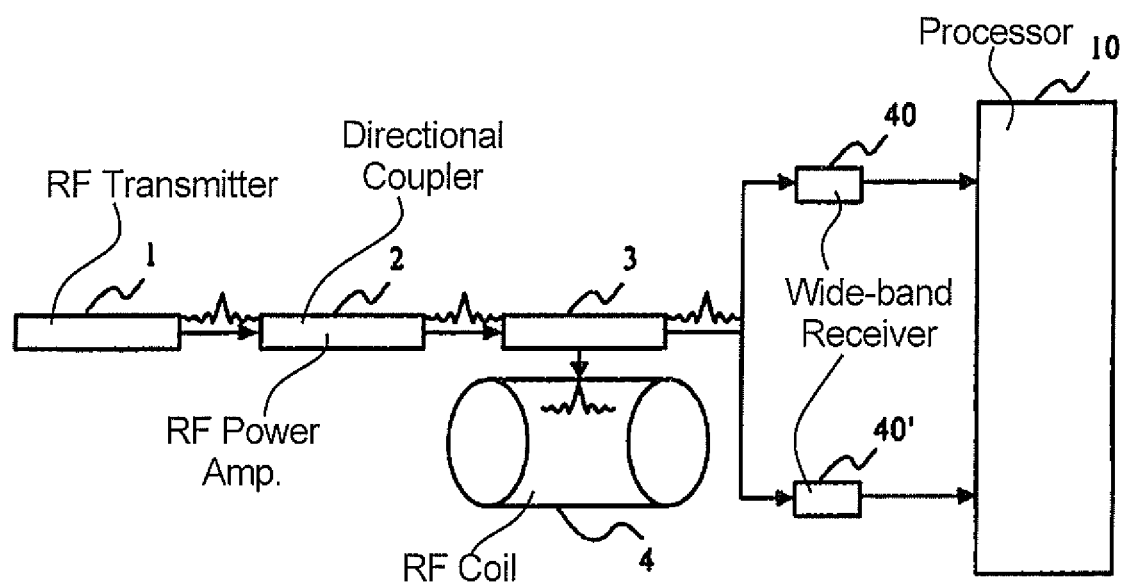
FIG. 4 is a block diagram of a second demonstrative application of the RF power calculation apparatus for an MRI system according to an embodiment of the present invention.

FIG. 4 is a block diagram of a second demonstrative application of the RF power calculation apparatus for an MRI system according to an embodiment of the present invention.

In FIG. 4, the RF power calculation processor 10 has two input signals; one input signal is an RF signal received from an analog front end by a first wide-band receiver 40 by a wide-band receiving method, the other input signal is an RF signal received from the analog front end by a second wide-band receiver 40' by another wide-band receiving method. The first wide-band receiver 40 and second wide-band receiver 40' may have identical or similar specific structures.

The RF transmitter 1 transmits RF signals in an analog signal format; the RF power amplifier 2 amplifies the RF signals in the analog signal format, and sends the amplified RF signals to the directional coupler 3; the directional coupler 3 sends most of the RF signals to an RF coil 4, so that the RF coil 4 transmits the RF signals. The directional coupler 3 also sends a small portion of RF signals to the first wide-band receiver 40 and the second wide-band receiver 40', to be used for subsequent power measurement.

An RF signal received by the first wide-band receiver 40 and an RF signal received by the second wide-band receiver 40' serve as input signals for the RF power calculation processor 10 shown in FIG. 2.

Assume that the RF signal received by the first wide-band receiver 40 is inputted to the first power calculation processor 11 of the RF power calculation processor 10, and that the RF signal received by the second wide-band receiver 40' is inputted to the second power calculation processor 12 of the RF power calculation processor 10. The first power calculation processor 11 of the RF power calculation processor 10 has a sliding average processing element, a non-linear correction element, and an RF power integral operation element. Similarly, the second power calculation processor 12 of the RF power calculation processor 10 has a sliding average processing element, a non-linear correction element, and an RF power integral operation element.

The RF signal received by the first wide-band receiver 40 passes through the sliding average processing element, non-linear correction element and RF power integral operation element of the first power calculation processor 11 in sequence. The sliding average processing element performs sliding average processing; the non-linear correction element performs non-linear correction; the RF power integral operation element calculates a power, i.e. a first power, of the RF signal received by the first wide-band receiver 40.

The RF signal received by the second wide-band receiver 40' passes through the sliding average processing element, non-linear correction element and RF power integral operation element of the second power calculation processor 12 in sequence. The sliding average processing element performs sliding average processing; the non-linear correction element performs non-linear correction; the RF power integral operation element calculates a power, i.e. a second power, of the RF signal received by the second wide-band receiver 40'.

A time correction unit of the RF power calculation processor 10 performs time correction on the first power and second power.

A difference calculation processor 13 calculates the difference m between the first power and second power which have undergone time correction. When the difference m is smaller than a pre-set first threshold K, an RF power calculation processor 14 calculates the average value of the first power and second power, the average value being a measurement value of the RF signal. When the average value of the first power and second power is greater than a pre-set second threshold G, the RF power calculation processor 14 sends a trigger signal to an alarm module. When the difference m is not smaller than a pre-set first threshold K, the difference calculation processor 13 sends a trigger signal to the alarm module.

Upon receiving the trigger signal sent by the RF power calculation processor 14, the alarm module issues to the user an alarm instruction indicating that the RF signal power does not conform to the safety specification. Moreover, upon receiving the trigger signal sent by the difference calculation processor 13, the alarm module issues to the user an alarm instruction indicating that RF signal reception is abnormal.

Figure 5:
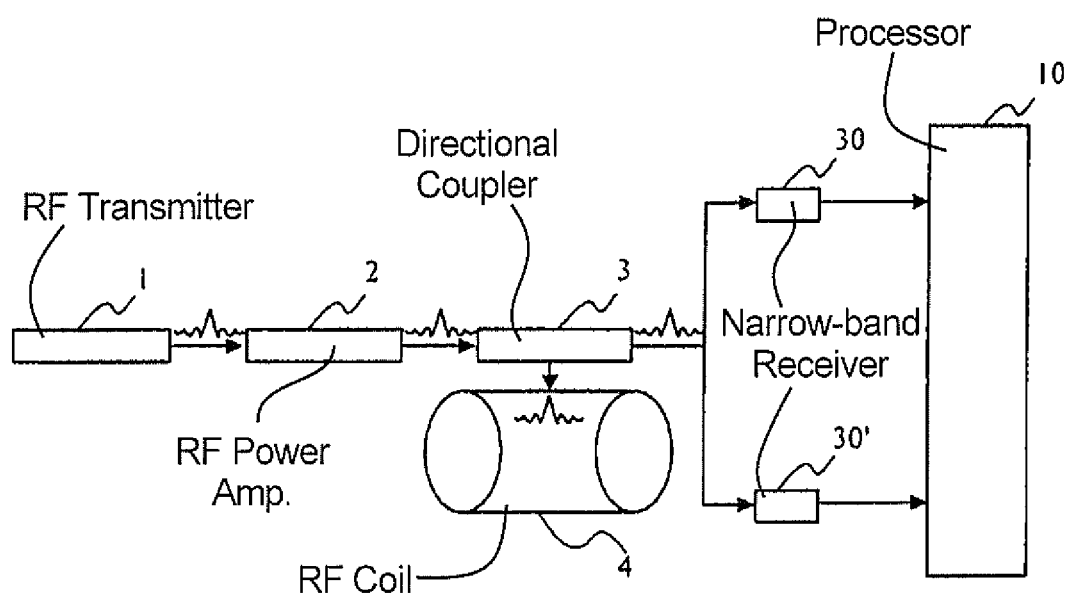
FIG. 5 is a block diagram of a third demonstrative application of the RF power calculation apparatus for an MRI system according to an embodiment of the present invention.

FIG. 5 is a block diagram of a third demonstrative application of the RF power calculation apparatus for an MRI system according to an embodiment of the present invention.

In FIG. 5, the RF power calculation processor 10 has two input signals; one input signal is an RF signal received from an analog front end by a first narrow-band receiver 30 by a narrow-band receiving method, the other input signal is an RF signal received from the analog front end by a second narrow-band receiver 30' by another narrow-band receiving method. The first narrow-band receiver 30 and second narrow-band receiver 30' may have identical or similar specific structures.

The RF transmitter 1 transmits RF signals in an analog signal format; the RF power amplifier 2 amplifies the RF signals in the analog signal format, and sends the amplified RF signals to the directional coupler 3; the directional coupler 3 sends most of the RF signals to an RF coil 4, so that the RF coil 4 transmits the RF signals. The directional coupler 3 also sends a small portion of RF signals to the first narrow-band receiver 30 and the second narrow-band receiver 30', to be used for subsequent power measurement.

RF signals received by the first narrow-band receiver 30 and the second narrow-band receiver 30' serve as input signals for the RF power calculation processor 10 shown in FIG. 2.

Assume that the RF signal received by the first narrow-band receiver 30 is provided as an input to the first power calculation processor 11, and that the RF signal received by the second narrow-band receiver 30' is inputted to the second power calculation processor 12. The first power calculation processor 11 of the RF power calculation processor 10 has a center frequency identification unit, a frequency compensation unit, a down conversion unit, and a power measurement value calculation unit. Similarly, the second power calculation processor 12 of the RF power calculation processor 10 has a center frequency identification unit, a frequency compensation unit, a down conversion unit, and a power measurement value calculation unit.

An RF signal received by the first narrow-band receiver 30 is provided as an input to the center frequency identification unit, frequency compensation unit, down conversion unit and power measurement value calculation unit of the first power calculation processor 11 in sequence. In the first power calculation processor 11: the center frequency identification unit identifies a center frequency of an RF signal; the frequency compensation unit performs frequency compensation on the RF signal whose center frequency has been identified; the down conversion unit performs down conversion on the RF signal that has undergone frequency compensation; and the power measurement value calculation unit calculates a power of the RF signal that has undergone down conversion. Specifically, the power measurement value calculation unit of the first power calculation processor 11 has an amplitude extraction element, a sliding average processing element, a non-linear correction element, and an RF power integral operation element. The amplitude extraction element extracts an amplitude from the RF signal; the sliding average processing element performs sliding average processing; the non-linear correction element performs non-linear correction; the RF power integral operation element calculates a power, i.e. a first power, of the RF signal received by the narrow-band receiving method.

An RF signal received by the second narrow-band receiver 30' is provided as an input to the center frequency identification unit, frequency compensation unit, down conversion unit and power measurement value calculation unit of the second power calculation processor 12 in sequence. In the second power calculation processor 12: the center frequency identification unit identifies a center frequency of an RF signal; the frequency compensation unit performs frequency compensation on the RF signal whose center frequency has been identified; the down conversion unit performs down conversion on the RF signal that has undergone frequency compensation; and the power measurement value calculation unit calculates a power of the RF signal that has undergone down conversion. Specifically, the power measurement value calculation unit of the second power calculation processor 12 has an amplitude extraction element, a sliding average processing element, a non-linear correction element, and an RF power integral operation element. The amplitude extraction element extracts an amplitude from the RF signal; the sliding average processing element performs sliding average processing; the non-linear correction element performs non-linear correction; the RF power integral operation element calculates a power, i.e. a second power, of the RF signal received by the narrow-band receiving method.

A time correction unit of the RF power calculation processor 10 performs time correction on the first power and second power. A difference calculation processor 13 calculates the difference m between the first power and second power which have undergone time correction. When the difference m is smaller than a pre-set first threshold K, an RF power calculation processor 14 calculates the average value of the first power and second power, the average value being a measurement value of the RF signal. When the average value of the first power and second power is greater than a pre-set second threshold G, the RF power calculation processor 14 sends a trigger signal to an alarm module. When the difference m is not smaller than a pre-set first threshold K, the difference calculation processor 13 sends a trigger signal to the alarm module.

Upon receiving the trigger signal sent by the RF power calculation processor 14, the alarm module issues to the user an alarm instruction indicating that the RF signal power does not conform to the safety specification. Moreover, upon receiving the trigger signal sent by the difference calculation processor 13, the alarm module 15 issues to the user an alarm instruction indicating that RF signal reception is abnormal.

In the embodiment described above, the RF power calculation apparatus has two input signals. In fact, the RF power calculation apparatus may also have three input signals, or an even greater number of input signals.

Figure 6:
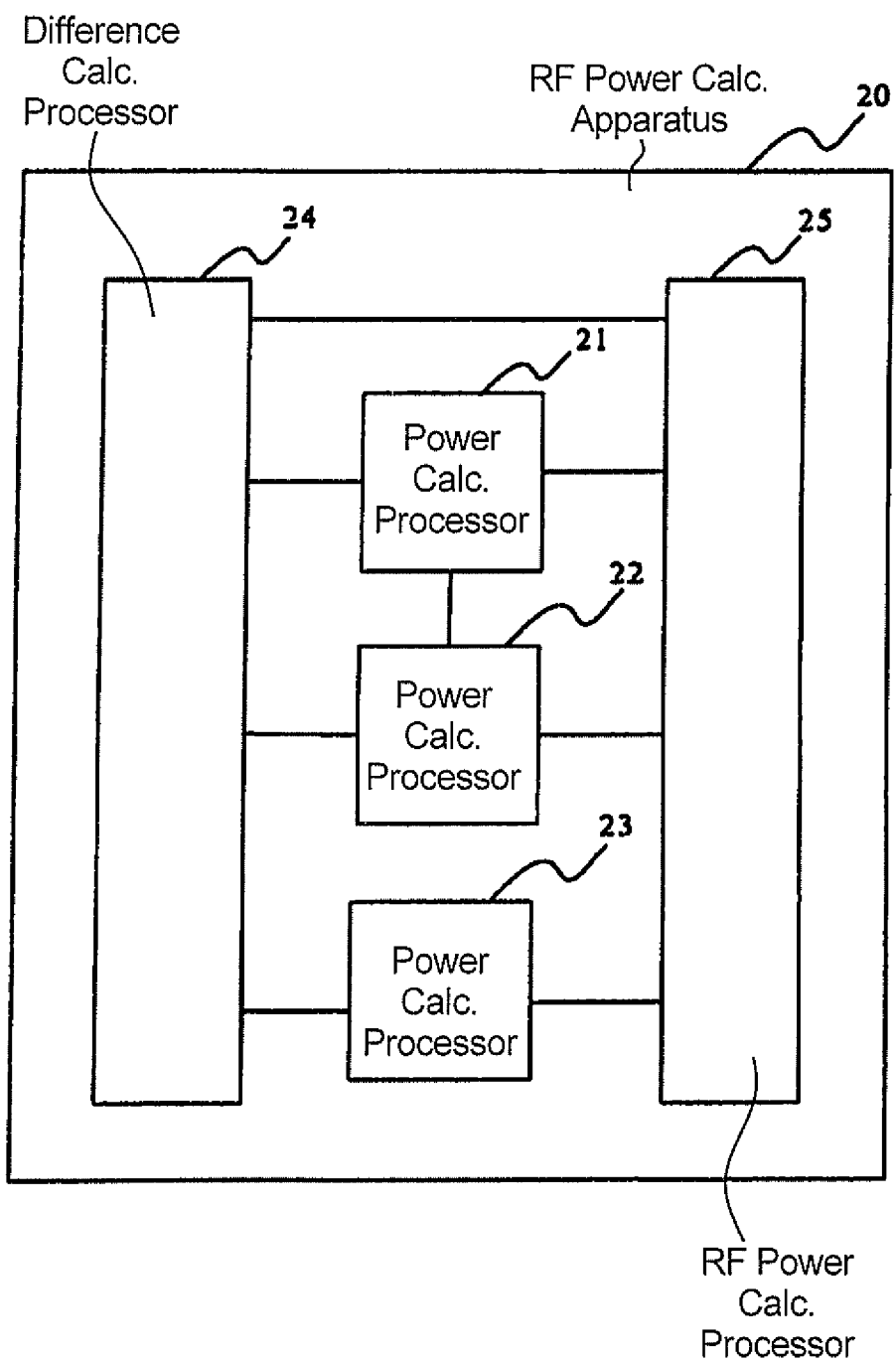
FIG. 6 is another block diagram of an RF power calculation apparatus for an MRI system according to an embodiment of the present invention.

FIG. 6 is another block diagram of an RF power calculation apparatus for an MRI system according to an embodiment of the present invention. In FIG. 6, the RF power calculation apparatus has three input signals.

As FIG. 6 shows, an RF power calculation apparatus 20 of the MRI system has:

a first power calculation processor 21 that calculates a first power of an RF signal received by a first receiving method;

a second power calculation processor 22 that calculates a second power of the RF signal received by a second receiving method;

a third power calculation processor 23 that calculates a third power of the RF signal received by a third receiving method;

a difference calculation processor 24 that calculates a first difference between the first power and second power, a second difference between the first power and third power, and a third difference between the second power and third power;

an RF power calculation processor 25 that calculates the average value of the first power, second power and third power when the first difference, second difference and third difference are all smaller than a pre-set first threshold. The average value is an RF power measurement value of the RF signal.

Figure 7:
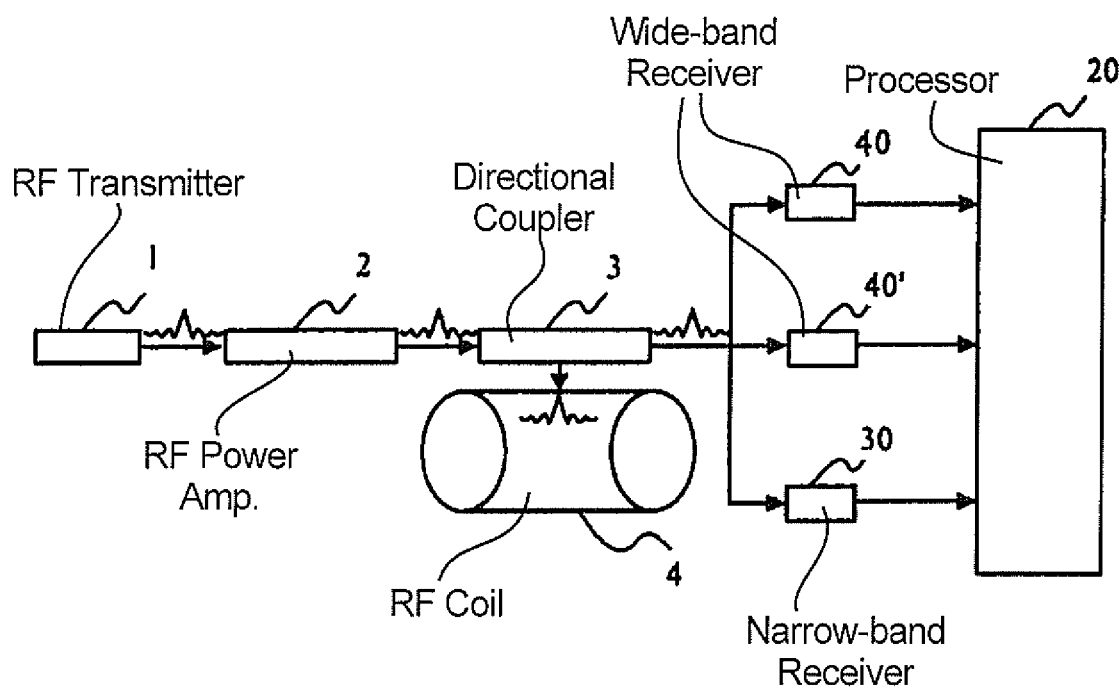
FIG. 7 is a fourth demonstrative block diagram of the RF power calculation apparatus for an MRI system according to an embodiment of the present invention.

FIG. 7 is a fourth demonstrative block diagram of the RF power calculation apparatus for an MRI system according to an embodiment of the present invention.

In FIG. 7, the RF power calculation apparatus 20 has three input signals; a first input signal is an RF signal received from an analog front end by a first wide-band receiver 40 by a wide-band receiving method; a second input signal is an RF signal received from the analog front end by a second wide-band receiver 40' by another wide-band receiving method; a third input signal is an RF signal received from the analog front end by a first narrow-band receiver 30 by a narrow-band receiving method.

The RF transmitter 1 transmits RF signals in an analog signal format; the RF power amplifier 2 amplifies the RF signals in the analog signal format, and sends the amplified RF signals to the directional coupler 3; the directional coupler 3 sends most of the RF signals to an RF coil 4, so that the RF coil 4 transmits the RF signals. The directional coupler 3 also sends a small portion of RF signals to the first wide-band receiver 40, the second wide-band receiver 40' and the first narrow-band receiver 30, to be used for subsequent power measurement.

RF signals received by the first wide-band receiver 40, the second wide-band receiver 40' and the first narrow-band receiver 30 serve as input signals for the RF power calculation apparatus 20 shown in FIG. 6.

Assume that the RF signal received by the first wide-band receiver 40 is provided as an input to the first power calculation processor 21 of the RF power calculation apparatus 20; that the RF signal received by the second wide-band receiver 40' is inputted to the second power calculation processor 22 of the RF power calculation apparatus 20; and that the RF signal received by the first narrow-band receiver 30 is provided as an input to the third power calculation processor 23 of the RF power calculation apparatus 20.

The first power calculation processor 21 has a sliding average processing element, a non-linear correction element, and an RF power integral operation element. Similarly, the second power calculation processor 22 has a sliding average processing element, a non-linear correction element, and an RF power integral operation element. The third power calculation processor 23 has a center frequency identification unit, a frequency compensation unit, a down conversion unit, and a power measurement value calculation unit. The power measurement value calculation unit has an amplitude extraction element, a sliding average processing element, a non-linear correction element, and an RF power integral operation element.

The RF signal received by the first wide-band receiver 40 passes through the sliding average processing element, non-linear correction element and RF power integral operation element of the first power calculation processor 21 in sequence. The sliding average processing element of the first power calculation processor 21 performs sliding average processing; the non-linear correction element of the first power calculation processor 21 performs non-linear correction; the RF power integral operation element of the first power calculation processor 21 calculates a power, i.e. a first power, of the RF signal received by the first wide-band receiver 40.

The RF signal received by the second wide-band receiver 40' passes through the sliding average processing element, non-linear correction element and RF power integral operation element of the second power calculation processor 22 in sequence. The sliding average processing element of the second power calculation processor 22 performs sliding average processing; the non-linear correction element of the second power calculation processor 22 performs non-linear correction; the RF power integral operation element of the second power calculation processor 22 calculates a power, i.e. a second power, of the RF signal received by the second wide-band receiver 40'.

The RF signal received by the first narrow-band receiver 30 is inputted to the center frequency identification unit, frequency compensation unit, down conversion unit and power measurement value calculation unit of the third power calculation processor 23 in sequence. The center frequency identification unit identifies a center frequency of an RF signal; the frequency compensation unit performs frequency compensation on the RF signal whose center frequency has been identified; the down conversion unit performs down conversion on the RF signal that has undergone frequency compensation; and the power measurement value calculation unit calculates a power of the RF signal that has undergone down conversion. Specifically, the power measurement value calculation unit comprises: an amplitude extraction element; a sliding average processing element; a non-linear correction element; and an RF power integral operation element. The amplitude extraction element extracts an amplitude from the RF signal; the sliding average processing element performs sliding average processing; the non-linear correction element performs non-linear correction; the RF power integral operation element calculates a power, i.e. a third power, of the RF signal received by the first narrow-band receiver 30.

A time correction unit of the RF power calculation apparatus 20 performs time correction on the first power, second power and third power, and sends the first power, second power and third power which have undergone time correction to the difference calculation processor 24.

The difference calculation processor 24 calculates the difference m1 between the first power and second power, the difference m2 between the first power and third power, and the difference m3 between the second power and third power. When the differences m1, m2 and m3 are all smaller than a pre-set first threshold K, the RF power calculation processor 25 calculates the average value of the first power, second power and third power, the average value being a measurement value of the RF signal. When the average value of the first power, second power and third power is greater than a pre-set second threshold G, the RF power calculation processor 25 sends a trigger signal to an alarm module. When at least one of the differences m1, m2 and m3 is not smaller than the pre-set first threshold K, the difference calculation processor 24 sends a trigger signal to the alarm module.

Upon receiving the trigger signal sent by the RF power calculation processor 25, the alarm module issues to the user an alarm instruction indicating to the user that the RF signal power does not conform to the safety specification. Moreover, upon receiving the trigger signal sent by the difference calculation processor 24, the alarm module issues to the user an alarm instruction indicating that RF signal reception is abnormal.

The RF power calculation apparatuses shown in FIGS. 2 to 7 may be implemented in more than one specific way, for example by a field programmable gate array (FPGA), a metal-oxide semiconductor field effect transistor (MOSFET) or a microprocessor system which supports ARM.

Based on the description above, the present invention also encompasses an RF power calculation method for an MRI system.

Figure 8:
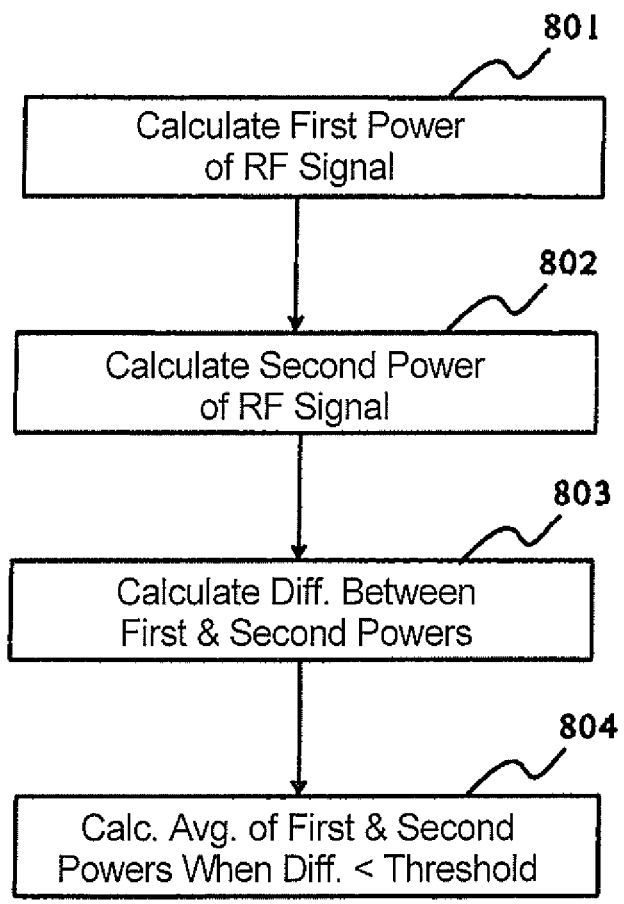
FIG. 8 is a first flowchart of an RF power calculation method for an MRI system according to an embodiment of the present invention.

FIG. 8 is a first demonstrative flowchart of an RF power calculation method for an MRI system according to an embodiment of the present invention.

As FIG. 8 shows, the method includes:

step 801: calculating a first power of an RF signal received by a first receiving method;

step 802: calculating a second power of an RF signal received by a second receiving method;

step 803: calculating the difference between the first power and second power;

step 804: calculating the average value of the first power and second power when the difference is smaller than a pre-set threshold.

In one embodiment, the first receiving method is a narrow-band receiving method, while the second receiving method is a wide-band receiving method.

Figure 9:
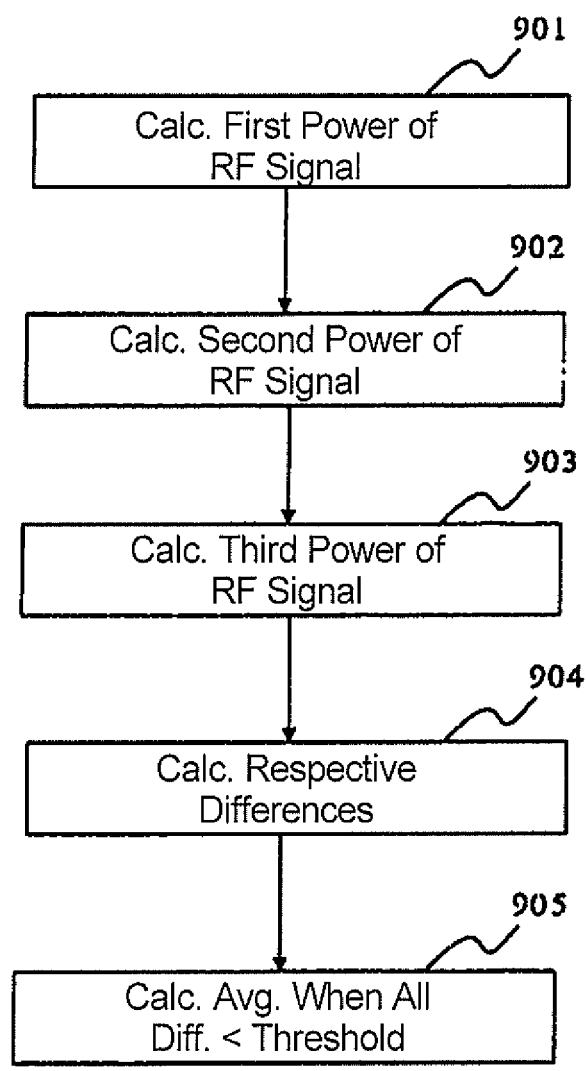
FIG. 9 is a second flowchart of an RF power calculation method for an MRI system according to an embodiment of the present invention.

FIG. 9 is a second demonstrative flowchart of an RF power calculation method for an MRI system according to an embodiment of the present invention.

As FIG. 9 shows, the method comprises:

step 901: calculating a first power of an RF signal received by a first receiving method;

step 902: calculating a second power of the RF signal received by a second receiving method;

step 903: calculating a third power of the RF signal received by a third receiving method;

step 904: calculating a first difference between the first power and second power, a second difference between the first power and third power, and a third difference between the second power and third power;

step 905: calculating the average value of the first power, second power and third power when the first difference, second difference and third difference are all smaller than a pre-set threshold.

In summary, in an embodiment of the present invention, a first power calculation module calculates a first power of an RF signal received by a first receiving method; a second power calculation module calculates a second power of the RF signal received by a second receiving method; a difference calculation module calculates the difference between the first power and second power; an RF power calculation module is used for calculating the average value of the first power and second power when the difference is smaller than a pre-set first threshold.

The present invention compares the difference between the first power and second power, and when the difference is smaller than a first threshold, calculates an RF power measurement value on the basis of the first power and second power, and so can improve the accuracy of calculation. Moreover, when the receiver is not operating normally and the power measurement value is not normal, an alert can be issued to the user promptly.

Furthermore, the present invention employs multiple digital processing methods in the course of RF signal reception and processing, therefore the performance requirements for the analog front end are significantly reduced, and costs can thereby be saved. Specifically, the present invention significantly reduces requirements regarding flatness of analog circuit frequency response, analog circuit linearity and degree of divergence in analog signal link delay times. For instance, it is possible, according to the actual application, to periodically adjust a correction parameter of the non-linear correction element, a center frequency of the center frequency identification unit and a frequency compensation factor of the frequency compensation unit, therefore the present invention can achieve high-precision calibration, so as to better meet user demands.

Furthermore, parameters in the process of receiving and processing RF signals in the present invention are preferably adjustable, so can be applied to more than one specific application environment.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A radio-frequency (RF) power calculation computer for a magnetic resonance imaging system, comprising:
    an input interface that receives an RF signal by a first receiving method and that also receives said RF signal by a second receiving method, said RF signal also being supplied to an RF coil of said magnetic resonance imaging system as an excitation signal that produces a magnetic resonance signal in an object;
    a first power calculation processor configured to calculate a first power of the RF signal received by said first receiving method;
    a second power calculation processor configured to calculate a second power of said RF signal received by said second receiving method;
    a difference calculation processor configured to calculate a difference between said first power and said second power; and
    an RF power calculation module configured to calculate an RF power of said RF signal from said first power and said second power when said difference is smaller than a first threshold, and to make the calculated RF power of said RF signal available from said RF power calculation processor as an electronic signal,
    wherein said first receiving method is a narrow-band receiving method and said second receiving method is a wide-band receiving method, and wherein said first power calculation processor comprises:
        a center frequency identifier configured to identify a center frequency of the RF signal;
        a frequency compensator configured to perform a frequency compensation on said RF signal of which the center frequency has been identified;
        a down converter configured to perform a down conversion on said RF signal that has been frequency compensated; and
        a power measurement module calculator configured to calculate, as said power of said RF signal, a power of the RF signal that has been down-converted.

2. A computer as claimed in claim 1 wherein said RF power calculation module is configured to calculate said RF power of said RF signal as an average of said first power and said second power, when said difference is smaller than said first threshold.

3. A computer as claimed in claim 1 comprising an alarm module configured to issue a first alarm instruction when said difference is greater than or equal to said first threshold, and to issue a second alarm instruction when said RF power is greater than a second threshold.

4. A computer as claimed in claim 1 wherein:
    said power measurement value calculator comprises an amplitude extraction element, a sliding average processing element, a non-linear correction element, and an RF power integral operation element; and
    said second power calculation module comprises a sliding average processing element, a non-linear correction element, and an RF power integral operation element.

5. A radio-frequency (RF) power calculation computer for a magnetic resonance imaging system comprising:
    an input interface that receives an RF signal with a first receiving method and that also receives said RF signal with a second receiving method and to also receive said RF signal with a third receiving method, said RF signal also being supplied to an RF coil of said magnetic resonance imaging system as an excitation signal that produces a magnetic resonance signal in an object;
    a first power calculation processor configured to calculate a first power of the RF signal received by said first receiving method;
    a second power calculation processor configured to calculate a second power of the RF signal received by said second receiving method;
    a third power calculation processor configured to calculate a third power of the RF signal received by said third receiving method;
    a difference calculation processor configured to calculate a first difference between said first power and said second power, a second difference between said first power and said third power, and a third difference between said second power and said third power; and
    an RF power calculation module configured to calculate an RF power of said RF signal based on said first power, said second power and said third power, when said first difference, said second difference and said third difference are all smaller than a first threshold,
    wherein said first receiving method is a wide-band receiving method, said second receiving method is a wide-band receiving method, and said third receiving method is a narrow-band receiving method, and wherein said third power calculation processor comprises:
        a center frequency identifier configured to identify a center frequency of the RF signal;
        a frequency compensator configured to perform a frequency compensation on said RF signal of which the center frequency has been identified;
        a down converter configured to perform a down conversion on said RF signal that has been frequency compensated; and
        a power measurement module calculator configured to calculate, as said power of said RF signal, a power of the RF signal that has been down-converted.

6. A radio-frequency (RF) power calculation method for a magnetic resonance imaging system, comprising:
    via an input interface of a computer, receiving an RF signal with a first receiving method and also receiving the RF signal with a second receiving method, said RF signal also being supplied to an RF coil of said magnetic resonance imaging system as an excitation signal that produces a magnetic resonance signal in an object;
    in a processor of said computer, calculating a first power of an RF signal received by the first receiving method;
    in a processor of said computer, calculating a second power of the RF signal received by the second receiving method;
    in a processor of said computer, calculating a difference between said first power and said second power; and
    in a processor of said computer, calculating an RF power of the RF signal based on said first power and said second power when said difference is smaller than a first threshold, and making the calculated RF power of the RF signal available from the processor as an electronic signal, wherein said first receiving method is a narrow-band receiving method and said second receiving method is a wide-band receiving method, and wherein said first power comprises:
  identifying a center frequency of the RF signal;
  frequency compensating said RF signal of which the center frequency has been identified;
  down converting said RF signal that has been frequency compensated; and
  calculating, as said power of said RF signal, a power of the RF signal that has been down-converted.

7. A radio-frequency (RF) power calculation method for a magnetic resonance imaging system, comprising:
  via an input interface of a computer, receiving an RF signal with a first receiving method and also receiving the RF signal with a second receiving method and also receiving the RF signal with a third receiving method, said RF signal also being supplied to an RF coil of said magnetic resonance imaging system as an excitation signal that produces a magnetic resonance signal in an object;
  in a processor of said computer, calculating a first power of the RF signal received by the first receiving method;
  in a processor of said computer, calculating a second power of the RF signal received by the second receiving method;
  in a processor of said computer, calculating a third power of the RF signal received by the third receiving method;
  in a processor of said computer, calculating a first difference between said first power and said second power, a second difference between said first power and said third power, and a third difference between said second power and said third power; and
  in a processor of said computer, calculating an RF power of the RF signal based on said first power, said second power and said third power, when said first difference, said second difference and said third difference are all smaller than a first threshold, and making the calculated RF power of the RF signal available from the computer as an electronic signal,
  wherein said first receiving method is a wide-band receiving method, said second receiving method is a wide-band receiving method, and said third receiving method is a narrow-band receiving method, and wherein calculating said third power comprises:
  identifying a center frequency of the RF signal;
  frequency compensating said RF signal of which the center frequency has been identified;
  down converting said RF signal that has been frequency compensated; and
  calculating, as said power of said RF signal, a power of the RF signal that has been down-converted.

* * * * *